US 6,572,614 B1

(12) United States Patent
Ellman et al.

(10) Patent No.: US 6,572,614 B1
(45) Date of Patent: Jun. 3, 2003

(54) BIPOLAR ARTHROSCOPIC PROBE

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/750,977

(22) Filed: Jan. 2, 2001

Related U.S. Application Data

(63) Continuation of application No. 09/728,382, filed on Dec. 4, 2000.

(51) Int. Cl.$^7$ ................................................ A61B 18/18
(52) U.S. Cl. .............................. 606/48; 606/33; 606/41
(58) Field of Search ........................... 606/32, 39, 40, 606/41, 45, 46, 47, 48, 49, 50

(56) References Cited

U.S. PATENT DOCUMENTS

| | | | | |
|---|---|---|---|---|
| 5,035,696 A | * | 7/1991 | Rydell | 606/47 |
| 5,403,311 A | * | 4/1995 | Abele et al. | 604/21 |
| 5,976,129 A | * | 11/1999 | Desai | 606/40 |
| 6,071,280 A | * | 6/2000 | Edwards et al. | 606/41 |
| 6,110,169 A | * | 8/2000 | Mueller et al. | 606/41 |

* cited by examiner

Primary Examiner—Linda C. M. Dvorak
Assistant Examiner—Henry M. Johnson

(57) ABSTRACT

A bipolar electrosurgical instrument that is configured for use in MIS and other electrosurgical procedures. The instrument is constructed as a bipolar electrode comprising a bare wire as the active electrode spaced from a window below which is the return electrode. The bare wire electrode preferably is configured as a straight wire projecting laterally from the distal end or with straight or curved sections that extend rearwardly toward the window. When energized, a bipolar discharge is generated between the active and return electrodes.

17 Claims, 2 Drawing Sheets

BIPOLAR ARTHROSCOPIC PROBE

RELATED APPLICATION

This application is a continuation-in-part of U.S. application, Ser. No. 09/728,382, filed Dec. 4, 2000, commonly owned, for "Bipolar Electrosurgical Handpiece For Treating Tissue", of which the present application is a continuation-in-part.

This invention relates to a bipolar electrosurgical probe for performing arthroscopic surgery.

BACKGROUND OF THE INVENTION

Our prior application, Ser. No. 09/728,382, and the applications to which it is related, describe electrosurgical electrodes and handpieces for treating tissue in a surgical procedure commonly known as minimally invasive surgery (MIS). Among the features described and claimed in the prior application is an electrosurgical handpiece that can be used in MIS and reduces the danger of excessive heat causing possible patient harm. This is achieved in one embodiment by an electrosurgical handpiece that is bipolar in operation and that is configured for use in MIS. The bipolar operation confines the electrosurgical currents to a small active region between the active ends of the bipolar electrode and thus reduces the possibility that excessive heat will be developed that can damage patient tissue. Moreover, the position of the active region can be controlled to avoid patient tissue that may be more sensitive to excessive heat. In a preferred embodiment, the flexible end is achieved by weakening at the end the housing for the electrode, and providing a pull string or wire connected to the weakened housing end and with a mechanism at the opposite end for the surgeon to pull the string or wire to flex the housing end to the desired position. This feature allows the surgeon to position the active electrode end at the optimum location for treating, say, a herniated disk to remove undesired regions and to provide controlled heat to shrink the tissue during surgery. In one of the prior applications referred to in the referenced application, a suitable bipolar electrode is described, which comprises a pair of rounded electrodes with spaced flat sides separated by an insulating layer. The referenced application describes a bipolar probe comprising substantially hemispherically-shaped active electrode segments spaced apart by a thin insulator.

There is a need in the art for rigid electrodes, i.e., without a flexible end, for treating orthopedic ailments, such as for example joint ailments of the shoulder, knee and hip, especially in a minimally invasive surgery (MIS) environment, also referred to from time to time as arthroscopy.

SUMMARY OF THE INVENTION

The present invention is a continuation-in-part of the referenced prior application and hereby incorporates by reference the total contents of it and its four related prior applications, Ser. Nos. 09/303,839, 09/393,286, 09/425,313, and 09/483,994. The present invention describes and claims among other things a bipolar electrode comprising an active electrode at the distal end of a rigid non-flexible handpiece. Since the present application otherwise makes use of the same teachings of the prior applications, it was felt unnecessary to repeat in the body of this specification many of the details present in the contents of the prior application. The present description will be confined solely to the modifications in the handpiece or electrode which will still achieve the same benefits as with the constructions of the prior applications. For more details, the reader is directed to the prior applications.

The new handpiece end constructions of the present improvement uses the bipolar principle and are configured to provide more controlled distribution of the electrosurgical currents to the tissue to be modulated. By "modulation" is meant ablation, cutting, smoothing, volumetric shrinkage, coagulation, hemostasis or cauterization.

In a preferred embodiment, the active electrode is formed by a projecting wire preferably extending laterally, or laterally and backwardly and connected to a first terminal of the bipolar source. The second terminal is connected to a return or ground electrode that is located rearward of the active electrode and is positioned on or inside of the handpiece but electrically accessible to electrosurgical currents emanating from the active electrode. The current path may include an electrically-conductive or semi-conductive fluid positioned between the active and return electrodes. The conductive fluid can be provided by an introduced fluid such as saline solution, or by body fluids normally present adjacent the tissue being modulated.

In a first preferred embodiment, the wire extends laterally, allowing its use as a cutting wire electrode and also as an ablative electrode. In a second preferred embodiment, the wire extends in a loop having a front section, a side section, and a rear section. The three sections are differently shaped allowing them to be used for different surgical purposes. By "laterally" is meant that the active electrode extend at right angles or at an acute angle, such as 45°, with respect to the longitudinal axis of the handpiece or the electrode shaft.

The constructions of the invention will provide the same important benefits not only for MIS of herniated disks but also for other MIS arthroscopic procedures where controlled electrode position and/or controlled heat generation is of importance as described in the prior applications, as well as for general electrosurgical procedures where the volumetric reduction of tissue or ablation of tissue is desirable.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals designating the same or similar elements.

DETAILED DESCRIPTION OF PREFERRED EMBODIMENTS

The reader is directed to the referenced prior applications for a more detailed description of the prior applications which will assist in understanding the improvements offered by the present application.

Figure 1:
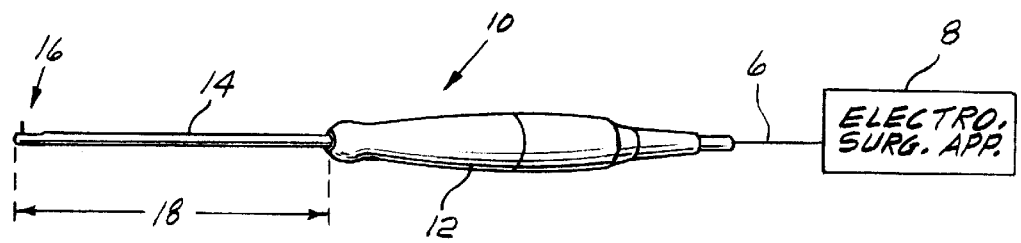
FIG. 1 is a schematic view of a bipolar electrode according to the invention mounted in a handle or handpiece.

In the present application, FIG. 1 is a schematic view of one form of electrosurgical instrument 10 in accordance with the invention. It comprises a rigid handle 12 with a conventional front end adapted to receive and hold rigidly the shank end (not shown) of an elongated support member 14 whose working end 16 is shown at the left. The support member 14 terminates in a distal end section 22 of reduced diameter. The handle 12 is electrically-insulating or if conductive covered with an electrically-insulating coating. Similarly, the shaft of the elongated support member 14 is also coated with an electrically-insulating coating, leaving bare the active electrode 20 at the working end 16 (See FIGS. 2 and 3). The support member 14 is long enough (see reference numeral 18) to extend through a conventional trocar or channel so that its working end 16 is exposed inside the patient. At the right end of the handle 12 is shown a cable 6 which contains two insulated wires for receiving bipolar electrosurgical currents from a conventional electrosurgical apparatus 8. The active parts of the bipolar electrode comprise a metal wire electrode 20 and a return or ground electrode 26 which is accessible via a window 24 in the insulated support member 14. As illustrated in FIG. 3, the cable 6 which extends through most of the handle and support member electrode comprises a first conductor 32 which is connected internally to the return electrode 26, and a second conductor 30 which is connected internally to the wire 20 via a channel shown schematically at 21. In this first embodiment, the active wire electrode 20 extends laterally of the longitudinal or long axis of the support member 14. Specifically, and preferably, it extends at an angle of 90° to the long axis. In the structure shown, all exposed surfaces are electrically-insulating, except for the active wire 20 and the return 26 which is accessible via the window 24. The end section 22 is made of electrically-insulating material. The support member body 14, from the dividing line 36 is coated with an electrically-insulating coating 38. As a result, part of the conductive ground 26 underlying the electrically-insulating coating 38 is not exposed to the outside, but, if a conductive or semi-conductive fluid is present, it will be able to access at least some of the conductive return underlying the coating 38. The two wires 30, 32 are not only insulated from each other so that bipolar electrosurgical voltages can be applied between them, but they are also insulated from the support member 14. In this description, by "axial" is meant parallel to the long axis of the support member 14 (horizontal in FIG. 3). By "lateral" is meant transverse to the long axis of the support member 14 (vertical in FIG. 3). "Lateral" is intended to include 90° for the embodiments of FIGS. 1–3, as well as an acute angle, such as 45°, for the embodiment of FIG. 5.

Once the surgeon has positioned the working end 16 of the instrument with respect to the tissue to be operated on, he or she then activates the electrosurgical apparatus 8 causing a discharge of bipolar currents between the active wire electrode 20 and the return electrode 26 capable of causing excision of or ablation of or shrinkage of tissue or cauterization of a blood vessel in the usual way. The active wire is best used as a needle electrode or with its front side passing over the tissue. As with the embodiments of the prior application, the insulating coating on the support member 14 will prevent accidental touching of patient tissue by the electrode sides, so that the bipolar discharge is locallized to the spacing between the bare parts 20, 26. The operation can take place in a wet field with a conductive or semi-conductive fluid completing the current path, or in a dry field where the electrosurgical currents from the active wire 20 seek out the closest return or ground which will be the electrode 26. The surgeon positions the electrode 20 so as to touch or pass lightly over the tissue to be modulated as needed for the procedure being followed.

For example, a suitable metal for the electrodes is brass, tungsten or stainless steel. The spacing 34 between the two electrodes can vary between 0.35–0.55 inches, preferably about 0.47 inches. The spacing 34 also happens to be the distance between the wire electrode 20 and the nearer edge of the window 24. The height 36 of the wire electrode 20 can vary between 0.06–0.1 inches, preferably about 0.08 inches. The width 38 of the insulated end can vary between 0.08–0.1 inches, preferably about 0.1 inches. The dimensions of the window 24 can vary between about 0.3–0.5×0.6–0.9 inches, preferably about 0.38×0.6 inches. The underlying conductive ground 26 will have about the same width dimension as the window, and extend in the length direction about 2–3 times longer than the window length. The depth of the conductive return or ground below the window surface is preferably about 0.023 inches. The overall length of the support member 14 typically will be about 3–8 inches.

Figure 2:
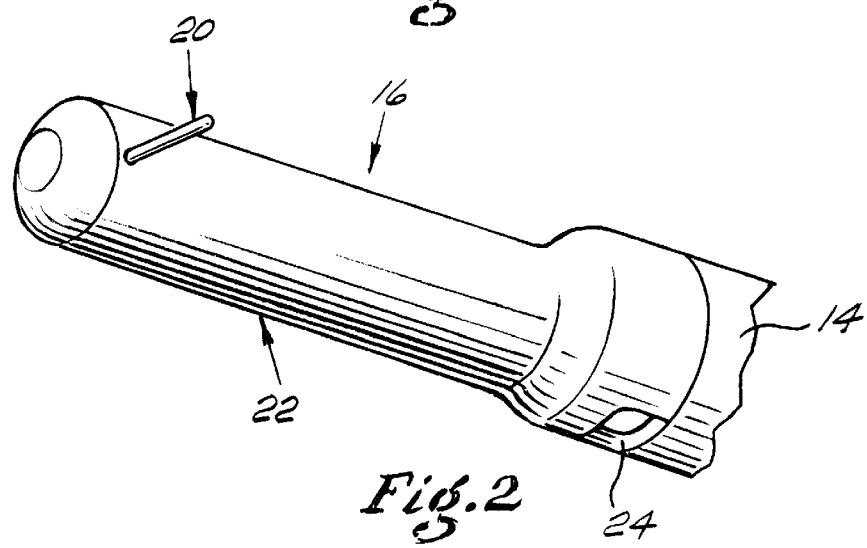
FIG. 2 is a perspective view of the active end of one form of bipolar electrode according to the invention.
Figure 3:
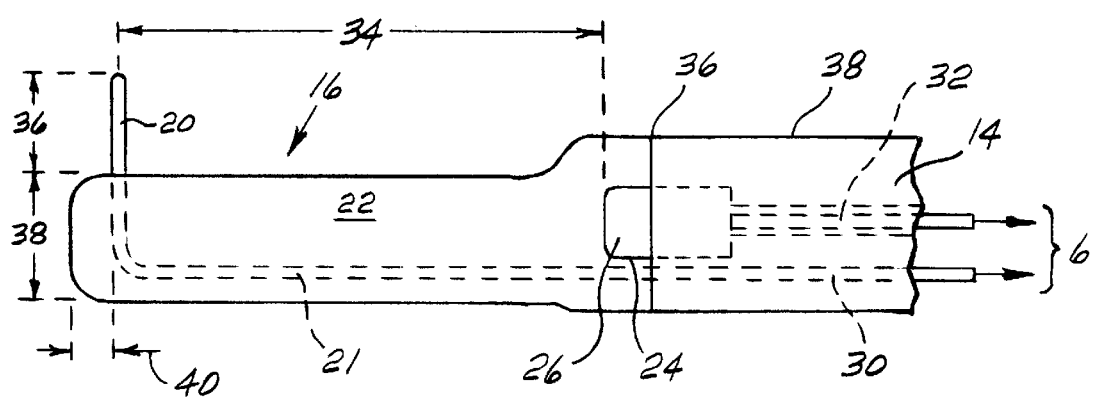
FIG. 3 is a side view of the electrode of FIG. 2.
Figure 4:
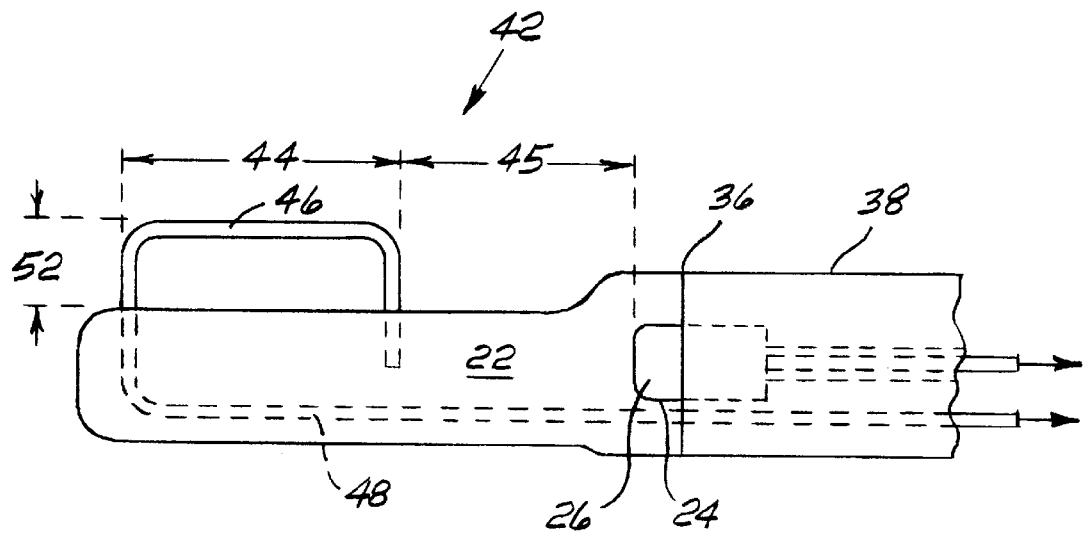
FIG. 4 is a side view similar to FIG. 3 of another bipolar electrode according to the invention.
Figure 5:
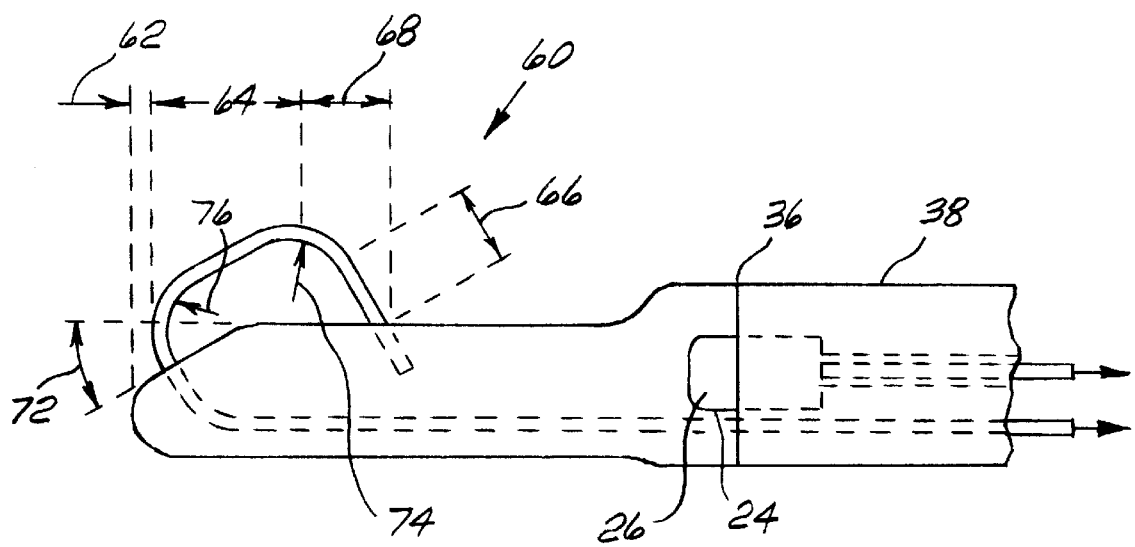
FIG. 5 is a side view similar to FIG. 3 of still a further bipolar electrode according to the invention.

FIGS. 1–3 illustrate a preferred embodiment of the invention in which the active wire electrode 20 is configured as a straight wire extending at right angles to the long axis of the support member 14. Both the point, as well as the side of the wire, can be used by the surgeon. FIGS. 4 and 5 show two other preferred embodiments of the invention involving an active wire in which only sides of the wire can be used to modulate the tissue. The rest of the electrode remains the same, except that some of the spacings and dimensions change.

In FIG. 4, the active wire electrode 46 is configured as a leading first section that extends at right angles to the long axis of the support member 14, a second mid-section that extends parallel to the long axis, and a trailing third section that also extends at right angles to the long axis of the support member 14. The corresponding preferred dimensions are: the first section has a height 52 of 0.03–0.07 inches, preferably about 0.05 inches; the second section has a length 44 of 0.2–0.3 inches, preferably about 0.24 inches; the third section has a height the same as that of the first section and is spaced 45 from the window edge of 0.15–0.25 inches, preferably about 0.2 inches. In this case, the front side of the first and the top side of the second section can be used for tissue modulation.

In FIG. 5, the active wire electrode 46 is configured as a leading curved first section that extends out at right angles from a sloped end surface of the end section 22 and bends rearward to form a second straight mid-section that extends roughly parallel to the sloped end surface of the end section 22 and then bends rearward to form a trailing curved third section followed by a short straight section before it ends embedded in the end section 22. The corresponding preferred dimensions are:

the end surface slopes to form an acute angle 72 of about 20–40°, preferably about 30°; the first section has a radius of curvature 76 of about 0.04–0.06 inches, preferably about 0.05 inches; the second section has a length 64 of 0.14–0.17 inches, preferably about 0.16 inches; the third section has a radius of curvature 74 approximately the same as that of the first section; and the fourth section has a length 66 of 0.03–0.07 inches, preferably about 0.05 inches. In this case, the front curved side of the first section, the outer straight side of the second section, the rear curved side of the third section, or the rearwardly-facing straight side of the fourth section can be used for tissue modulation. For example, the curved sections can serve to cut or shave or smooth tissue, the straight sections to shave or smooth tissue, the third curved section for point coagulation of bleeders, and the fourth straight section for cutting. Thus, this electrode configuration offers the most flexibility to the surgeon in his or her choice of modulating surfaces. Where the end of the fourth section embeds in the holder can be spaced about the same distance from the window edge as 45 of FIG. 2.

Other usable mechanical or electrical structures following the teachings of the prior applications when combined with that of the present application will be appreciated by those skilled in this art.

The electrosurgical apparatus 8 preferably is an ultra high frequency (RF) radiosurgical energy source, which operates in the range of about 1.5–4 MHz. Studies have shown that the 1.5–4 MHz frequency range is the preferred RF energy to incise and coagulate tissue, generally modulate tissue, because tissue thermal necrosis is minimal and, when interfaced with the electrosurgical electrode of the invention, provides excellent cutting, smoothing and hemostasis especially for joint orthopedic procedures. An example of suitable electrosurgical apparatus is the Model SURGITRON Dual-Frequency electrosurgical unit manufactured by and available from Ellman International, Inc. of Hewlett, N.Y.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A bipolar electrosurgical electrode for treating orthopedic ailments comprising:
   (a) an axially elongated support first member (14) of electrically-insulating material and having a proximal first portion and a distal second end portion (22),
   (b) first and second electrically-conductive wires (6) positioned in electrically-insulating relationship in the first member with first means connected to the first member at its first portion for applying to the first and second wires a bipolar electrosurgical voltage capable of generating electrosurgical currents, one of the first and second electrically-conductive wires leading to a distal bare wire (20, 46) configured to project out of the first member (14) at its second end portion (22) and serving as the active electrode of a bipolar system,
   (c) a side window (24) in the second end portion (22) of the first member axially spaced rearwardly of the bare wire,
   (d) a conductor (26) located within the first member and having a bare surface exposed within the side window and connected to the other of the first and second electrically-conductive wires and serving as the return electrode of the bipolar system,
   (e) wherein electrosurgical currents are generated between the projecting bare wire and the return electrode in the side window when the electrosurgical voltage is applied to the first and second wires.

2. The bipolar electrosurgical electrode as claimed in claim 1, wherein the first member (14) has a long axis, the active electrode comprises a rigid bare wire (20) extending outwardly at right angles to the long axis.

3. The bipolar electrosurgical electrode as claimed in claim 2 wherein the bare wire (20) of the active electrode is straight.

4. The bipolar electrosurgical electrode as claimed in claim 3 wherein the side window has an edge nearest to the bare wire (20) of the active electrode, the bare wire of the active electrode being is spaced (34) from the nearest window edge about 0.35–0.55 inches.

5. The bipolar electrosurgical electrode as claimed in claim 3 wherein the bare wire electrode has a height (36) in the right angle direction of about 0.06–0.1 inches, the side window is rectangular with a short dimension of about 0.3–0.5 inches and a long dimension of about 0.6–0.9 inches.

6. The bipolar electrosurgical electrode as claimed in claim 1, wherein the first member (14) has a long axis, the active electrode (46) comprises a rigid bare wire having a first section extending outwardly at right angles to the long axis, a second section extending rearwardly parallel to the long axis, and a third section extending inwardly at right angles to the long axis.

7. The bipolar electrosurgical electrode as claimed in claim 6 wherein the first, second and third sections of the bare wire of the active electrode are straight.

8. The bipolar electrosurgical electrode as claimed in claim 7 wherein the side window has an edge nearest to the third section of the bare wire (46) of the active electrode, the third section of the bare wire of the active electrode being spaced from the nearest window edge about 0.15–0.25 inches.

9. The bipolar electrosurgical electrode as claimed in claim 8 wherein the bare wire electrode has a height (52) of the first and third sections of the bare wire electrode in the right angle direction of about 0.03–0.07 inches, the side window is rectangular with a short dimension of about 0.3–0.5 inches and a long dimension of about 0.6–0.9 inches.

10. The bipolar electrosurgical electrode as claimed in claim 9 wherein the length (44) of the second section of the bare wire electrode is 0.2–0.3 inches, and each of the first, second and third sections can serve to modulate tissue.

11. The bipolar electrosurgical electrode as claimed in claim 1, wherein the first member (14) has a long axis, the active electrode comprises a rigid bare wire having a first curved section extending outwardly to the long axis, a second section extending rearwardly and outwardly to the long axis, a third curved section extending inwardly to the long axis, and a fourth straight section intersecting the first member (14).

12. The bipolar electrosurgical electrode as claimed in claim 11 wherein the side window has an edge nearest to the fourth section of the bare wire of the active electrode, the fourth section of the bare wire of the active electrode being spaced from the nearest window edge about 0.15–0.25 inches.

13. The bipolar electrosurgical electrode as claimed in claim 12 wherein the radius of curvature (76, 74) of the first and third sections of the bare wire electrode is between 0.04–0.06 inches.

14. The bipolar electrosurgical electrode as claimed in claim 13 wherein second section has a length (64) of 0.14–0.17 inches.

15. The bipolar electrosurgical electrode as claimed in claim 14 wherein the fourth section of the bare wire electrode has a length (66) between 0.03–0.07 inches.

16. In combination:
   (I) an electrosurgical energy source having a bipolar outlet;
   (II) an electrosurgical handpiece comprising:
      (a) an axially elongated support first member (14) of electrically-insulating material and having a proximal first portion and a distal second end portion (22), (b) first and second electrically-conductive wires (6) positioned in electrically-insulating relationship in the first member with first means connected to the first member at its first portion for applying to the first and second wires a bipolar electrosurgical voltage capable of generating electrosurgical currents, one of the first and second electrically-conductive wires leading to a distal bare wire (20, 46) configured to project out of the first member (14) at its second end portion (22) and serving as the active electrode of a bipolar system, (c) a side window (24) in the second end portion (22) of the first member axially spaced rearwardly of the bare wire, (d) a conductor (26) located within the first member and having a bare surface exposed within the side window and connected to the other of the first and second electrically-conductive wires and serving as the return electrode of the bipolar system, (III) means for connecting the first and means to the bipolar outlet of the electrosurgical energy source;

wherein electrosurgical currents are generated between the active and return electrodes when an electrosurgical voltage from the electrosurgical energy source is applied to the first and second wires.

17. The combination of claim 16, wherein the electrosurgical voltage is at a frequency of about 1.8–4 MHz.

* * * * *